(12) United States Patent
Lasenby et al.

(10) Patent No.: US 9,204,824 B2
(45) Date of Patent: Dec. 8, 2015

(54) METHOD AND APPARATUS FOR MONITORING AN OBJECT

(75) Inventors: Joan Lasenby, Hardwick (GB);
Jonathan Cameron, Grantchester (GB);
Richard Wareham, Cambridge (GB)

(73) Assignee: Pneumacare Limited, Ely, Cambridgeshire ( * ) Notice: Subject to any disclaimer, the term of this patent is extended or adjusted under 35 U.S.C. 154(b) by 619 days.

(21) Appl. No.: 13/487,948

(22) Filed: Jun. 4, 2012

(65) Prior Publication Data

US 2013/0002832 A1   Jan. 3, 2013

Related U.S. Application Data

(63) Continuation of application No. 13/157,672, filed on Jun. 10, 2011, now abandoned, which is a continuation of application No. PCT/EP2009/066790, filed on Dec. 10, 2009.

(51) Int. Cl.
*H04N 13/04* (2006.01)
*A61B 5/11* (2006.01)
(Continued)

(52) U.S. Cl.
CPC ............ *A61B 5/1128* (2013.01); *A61B 5/0064* (2013.01); *A61B 5/0077* (2013.01); *A61B 5/0816* (2013.01); *A61B 5/113* (2013.01);
(Continued)

(58) Field of Classification Search
CPC ........... G01N 21/95607; G06T 7/0012; H04N 13/0253; H04N 5/2258; H04N 13/0203; A61B 5/0077; A61B 6/4266; A61B 5/0064; A61B 5/1128; A61B 5/113; A61B 5/1135; G01B 11/25; G01B 11/2513

USPC .................. 348/51, 77; 382/128; 600/534
See application file for complete search history.

(56) References Cited

U.S. PATENT DOCUMENTS

2006/0233430 A1 * 10/2006 Kimura ..................... 382/128
2007/0171225 A1 *  7/2007 Haex et al. ................ 345/473
(Continued)

FOREIGN PATENT DOCUMENTS

DE         4402414       8/1994
EP      00919184 A1      6/1999
(Continued)

OTHER PUBLICATIONS

Lewis "Measuring the human chest with structured lighting".*
Gorini, M., et al., "Chest wall hyperinflation during acute bronchoconstriction in asthma," AM. J. Resp. Critic. Care Med., 160:808-816, 1999.
(Continued)

*Primary Examiner* — Andy Rao
*Assistant Examiner* — Jared Walker
(74) *Attorney, Agent, or Firm* — Ober, Kaler, Grimes & Shriver; Royal W. Craig

(57) ABSTRACT

A method and system of monitoring an object (e.g., for change in configuration of a person) includes projecting a radiation pattern onto the object; recording at a first time first image data representing a portion of the projected radiation pattern on the object, the first image data representative of a three dimensional configuration of the object at the first time; recording at a second time second image data representing a portion of the projected pattern of radiation on the object, the second image data representative of a three dimensional configuration of the object at the second time; and processing the first and second image data to generate differential data representative of a change in the configuration of the object between the first and second times.

29 Claims, 5 Drawing Sheets

(51) Int. Cl.
 A61B 5/00 (2006.01)
 A61B 5/08 (2006.01)
 A61B 5/113 (2006.01)
 G01B 11/16 (2006.01)
 G01B 11/25 (2006.01)
 G06T 7/00 (2006.01)
 H04N 13/02 (2006.01)

(52) U.S. Cl.
 CPC .............. *A61B5/1135* (2013.01); *G01B 11/16* (2013.01); *G01B 11/2513* (2013.01); *G06T 7/0012* (2013.01); *H04N 13/0203* (2013.01)

(56) References Cited

U.S. PATENT DOCUMENTS

2009/0250631 A1* 10/2009 Feke et al. .................. 250/459.1
2010/0284591 A1* 11/2010 Arnon et al. ................ 382/128

FOREIGN PATENT DOCUMENTS

| EP | 01350466 | A1 | | 10/2003 | |
|---|---|---|---|---|---|
| EP | 1350466 | A1 | * | 10/2003 | ............... A61B 5/11 |
| EP | 1645840 | A1 | | 4/2006 | |
| EP | 01645841 | A1 | | 4/2006 | |
| GB | 2254691 | A | | 10/1992 | |
| JP | 20189389 | A | | 7/2000 | |
| WO | 0072748 | A1 | | 12/2000 | |
| WO | 0182785 | A2 | | 11/2001 | |
| WO | 02075245 | A1 | | 9/2002 | |
| WO | 2007142267 | A1 | | 12/2007 | |

OTHER PUBLICATIONS

Landelli, I., et al., "Determinants of exercise performance in normal men with externally imposed expiratory flow-limitation," J.Appl. Physiol., 92(5): 1943-1952, 2002.

Aliverti, A., et al., "Effects of bronchodilators on subdivisions of lung and chest wall volume in COPD," Eur. Respir. J., 20, suppl. 38, 13s 2002.

Dellaca, RL., et al., "Estimation of end-expiratory lung volume variations by optoelectronic plethysmography," Crit. Care Med., 29(9): 1807-11, 2001.

Aliverti, A., et al., "Human respiratory muscle actions and control during exercise," (1997) J Appl Physiol., 83: 1256-1269.

Lewis, J.R.T., et al., "Measuring The Human Chest With Structured Lighting," Pattern Recognition Letters, 1986, vol. 4, pp. 359-366.

Aliverti, A., et al., "Opto-electronic plethysmograph in intensive care patients," AM. J Resp. Crit. Care Med., 161: 1546-1552, 2000.

Aliverti, A., et al., "Regional Chest Wall Volumes during exercise in Chronic Obstructive Pulmonary Disease," Thorax 2004; 59: 210-216; downloaded from thorax.bmj.com on Mar. 22, 2012—Published by group.bmj.com—www.thoraxjnl.com.

Aliverti, A., et al., "Respiratory muscle dynamics and control during exercise with externally imposed expiratory flow-limitation," J. Appl. Physiol., 92(5): 1953-1963, 2002.

Kenyon, CM, et al., "Rib cage mechanics during quiet breathing and exercise in humans," (1997), J Appl Physiol., 83: 1242-1255.

Ferrigno, G., et al, "Three-dimensional optical analysis of chest wall motion," (1994) J Appl Physiol, 77: 1224-1231.

Cala, SJ, et al., "Chest Wall and lung volume estimation by optical reflectance motion analysis," (1996) J Appl Phsiol 81: 2680-2689.

* cited by examiner

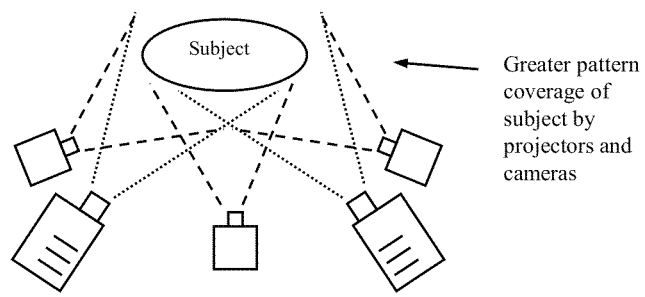
FIG. 6
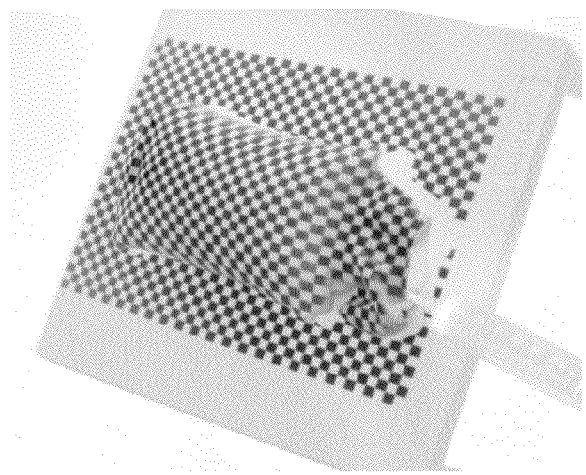
FIG. 7
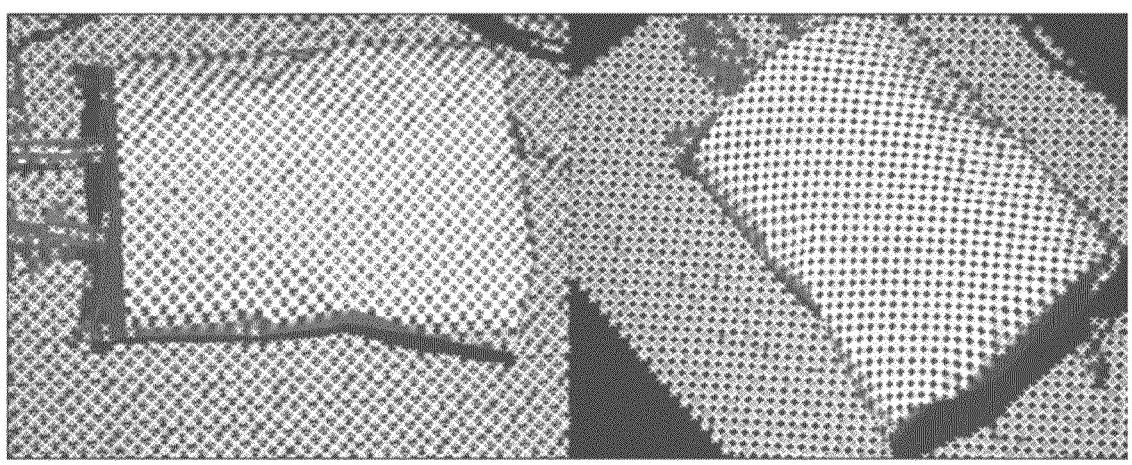
FIG. 8A                                   FIG. 8B

METHOD AND APPARATUS FOR MONITORING AN OBJECT

REFERENCE TO RELATED APPLICATIONS

This application is a continuation of U.S. Ser. No. 13/157,672 filed Jun. 10, 2011, which is a continuation of PCT/EP2009/066790 Filed Dec. 10, 2009.

FIELD OF THE INVENTION

The present invention relates to a method of monitoring an object and in particular, but not limited to, monitoring a change in configuration of a person.

BACKGROUND OF THE INVENTION

There are many applications where monitoring of a three dimensional configuration of an object can be implemented, for example monitoring of vital signs, including breathing and/or lung function of a person. In addition, monitoring of lung function can provide data which can be used to assist in determining the presence of lung disease which is a global health problem affecting millions of people. Effective medical management of lung disease requires assessment and monitoring of lung function. This is carried out largely by clinical observation or by spirometry (a technology developed in the 1930s).

There are restrictive limitations to present technologies for monitoring lung function, which fail to satisfy clinical needs; in particular, spirometry techniques require alert and co-operative patients to follow instructions whilst using an apparatus. These techniques are not suitable for use on children under 5 years old, for critically ill or unconscious patients, or for the chronically sick or elderly. Such patients often cannot be assessed or monitored fully, leaving assessment to subjective clinical observation. This leaves a subjective element to clinical decisions, for example a patient's transfer from intensive care to less resource-intensive general care or vice versa, resulting in inefficient use of resources and sub-optimal clinical management.

Other techniques for monitoring lung function require physical contact with the patient, for example requiring sensors or reflective markers to be placed on or attached to the subject. This may be medically inadvisable or impossible, for example in critical care situations such as the monitoring of a burns victim, or the measurement of lung function in premature babies.

It is an object of the invention to overcome such disadvantages.

SUMMARY OF THE INVENTION

In accordance with one aspect of the present invention, there is provided a method of monitoring an object, the method including:

a) projecting a pattern of radiation onto an object for monitoring;

b) recording at a first instant in time first image data representing at least a portion of said projected pattern of radiation on the object, said first image data being representative of a three dimensional configuration of said object at said first instant in time;

c) recording at a second instant in time second image data representing at least a portion of said projected pattern of radiation on the object, said second image data being representative of a three dimensional configuration of said object at said second instant in time; and d) processing said first and second image data to generate differential data representative of a change in the configuration of said object between the first and second instants in time.

The method of the invention advantageously provides for monitoring changes of three dimensional configuration of an object accurately over a period of time. By using the projected pattern of radiation to obtain corresponding image data for use in generating the differential data, it is not required for any contact with the object being monitored to be made. Accordingly, the method of the present invention is simple to effect, and is well suited for monitoring moving and/or delicate objects, including objects in controlled or isolated environments, since no contact with the object is required for its monitoring; the interaction with the object is in the form of the projected light pattern on the object.

Since the differential data is based upon first and second image data which represents a three dimensional configuration of the object, and therefore corresponds with the three dimensional nature of the object being monitored, the change in configuration of the object is determined accurately using the method of the invention.

In a preferred embodiment of the present invention the method includes processing said first and second image data to generate differential data representative of a change in volume of said object between the first and second instants in time. The ability to determine a change in volume of the object, over a period of time, without necessitating contact with the monitored object is advantageous and simple, and provides volume data of the object which may be used in many various applications.

The portions in steps b) and c) may be substantially the same portion of the pattern. Alternatively, the portions in step b) and c) are different portions of the pattern, allowing the method to generate the differential data for at least part of the object, whilst allowing movement of the object.

In one embodiment of the present invention the method includes processing of the first and second image data to identify gross movement of the object over time between the first and second time instants.

Preferably, the pattern of radiation is a spatially-varying intensity pattern of non-ionising electromagnetic radiation which, when interpreted as an image, comprises a combination of distinct and readily locatable elements, for example, combinations of spatial distributed crossing points, corners or circular patches.

Preferably the electromagnetic radiation may be visible light or non-visible infra-red radiation. Alternatively the electromagnetic radiation may be of other frequencies.

Preferably, in step a) a sequence of different patterns of radiation is projected onto the object, each of the different patterns being projected consecutively at a different instant in time.

In a preferred embodiment of the present invention the method includes:

recording further image data representing at least a portion of the projected pattern of radiation on the object at a plurality of further instants in time, said further image data being representative of a three dimensional configuration of said object at each of the plurality of further instants in time;

processing said further image data to generate differential data representative of a change in the configuration of said object between at least two of said plurality of further instants in time.

Recording and processing the further image data may be performed after recording and processing the first and second image data. The further image data may include a plurality of image data recorded respectively at a plurality of different instants in time. Differential data generated using the further image data may therefore be used to monitor the configuration change over a period of time of any duration, such as a prolonged period of time. This is advantageous, for example in medical applications of the invention such as continuous monitoring of the breathing of a patient over time.

The further image data may be recorded at rates consistent with a given application of the invention, dependent upon on the time resolution required for monitoring changes in the three dimensional configuration of an object. In a preferred embodiment for a medical application, for example monitoring of chest movement and breathing, this rate may be 50 or 60 instants in time per second, i.e. 50 or 60 Hertz. Alternatively, the further image data may be recorded at a faster rate, for example 180 or 360 instants per second, providing enhanced time resolution and spatial accuracy. Any recording rate may be selected so that the change in configuration of the object can be monitored as desired; for example, but not limited to a rate within the range of 50 to 360 Hertz. The rate may be determined by the capabilities and/or settings of the apparatus performing the monitoring, such as of the camera.

In a preferred embodiment the method includes approximating the configuration of a portion of the object upon which the pattern of radiation is not projected. The first and/or second image data may be used for the approximating. Additionally, or alternatively, an algorithm may be used to approximate the surface of the object upon which the intensity pattern is not projected. For example, a simple interpolation algorithm for a flat surface may be used. Alternatively a more complex algorithm may be used, to interpolate using a more complex surface, for example, a part of a cylinder or sphere. The method may include generating the differential data using the approximated configuration of the portion of the object. Accordingly, the configuration of a non scanned part of the object allows the change of configuration, for example a volume, to be accurately determined without requiring contact with the object by apparatus performing the invention method. The part of the object for which the configuration is approximated may be the reverse side of the object on which the radiation pattern is projected upon. For example, if the pattern is projected upon a front side of a person, the configuration of the rear side of the person may be approximated.

In embodiments of the invention the object is a person or at least a portion of a person. In such embodiments the method may include processing the first and second image data with bio-physical model data characterising the person. The bio-physical model data may include parameters representative of any of size, age, sex and body type of the person, and/or parameters representative of mechanical aspects of parts of the body. The parameters may relate to both normal and abnormal conditions of the person. This allows the method to be tuned to the body type of the person being monitored to yield enhanced accuracy of differential data.

In preferred embodiments the change of configuration may be indicative of a lung function of the person, such as breathing rate, dynamic air flow, and/or the dynamic change in breathing volume.

Patent application EP 1645841 describes a three dimensional shape measurement apparatus, but this does not record first and second image data according to the present invention, each being representative of a three dimensional configuration of an object being monitored. Therefore, it does not generate differential data using the first and second image data, as in the present invention. Moreover, the apparatus of the EP 1645841 requires precise positioning of apparatus components, unlike the apparatus of the present invention.

In a preferred embodiment the method further includes calibrating of apparatus arranged to perform at least steps a) and b), said calibrating including:

projecting a calibration pattern of radiation onto a calibration object; and recording calibration image data representing at least a portion of said projected calibration pattern of radiation, said calibration image data being representative of a three dimensional configuration of said calibration object, and processing said first and second image data in step d) with the calibration image data to generate the differential data.

Calibrating the apparatus advantageously ensures that the differential data generated is more accurate.

The method may include projecting a sequence of different calibration patterns of radiation onto the calibration object and recording the calibration image data for each of said different calibration patterns of radiation.

In embodiments of the invention, the method may include performing said calibrating before performing steps a) to d) to determine a unit scale for use in determining dimensions of the object from the first and/or second image data.

Preferably, the projecting in step a) further includes projecting said calibration pattern, or at least one of said calibration patterns onto the object for monitoring, and the first and/or second image data recorded in steps b) and/or c) includes calibration image data representative of characteristics of a projection system and recording system of apparatus for performing said method.

The projected pattern of radiation and the projected calibration pattern or at least one of the calibration patterns of radiation may be interleaved with each other. In this way calibrating may be performed simultaneously as monitoring the object.

In accordance with a further aspect of the present invention there is provided a method of monitoring an object, the method including:

a) projecting a pattern of radiation onto an object for monitoring;

b) recording at a first instant in time first image data representing at least a portion of said projected pattern of radiation on the object, said first image data being representative a three dimensional configuration of said object at said first instant in time;

c) recording at a second instant in time second image data representing at least a portion of said projected pattern of radiation on the object, said second image data being representative of a three dimensional configuration of said object at said second instant in time; and d) providing said first and second image data to a processing system for generating differential data representative of a change in the configuration of said object between the first and second instants in time.

In accordance with a yet further aspect of the present invention there is provided a method of monitoring an object, the method including:

a) receiving first and second image data recorded by the method of:

i) projecting a pattern of radiation onto an object for monitoring;

ii) recording at a first instant in time the first image data which represents at least a portion of said projected pattern of radiation on the object, said first image data being representative of a three dimensional configuration of said object at said first instant in time; and iii) recording at a second instant in time the second image data representing at least a portion of said projected intensity pattern of radiation on the object, said second image data being representative of a three dimensional configuration of said object at said second instant in time, and b) processing said first and second image data to generate differential data representative of a change in the configuration of said object between the first and second instants in time.

Accordingly, steps a) to c) of the method of the invention may be performed remotely from step d) of the invention, for example via a computer network.

In accordance with another further aspect of the present invention there is provided computer software arranged to perform the method according to the method of the present invention.

In accordance with yet a further aspect of the present invention there is provided a data carrier storing the computer software of the present invention.

In accordance with a further aspect of the present invention there is provided an apparatus for monitoring an object, the apparatus comprising:

a projection system arranged to project a pattern of radiation onto an object for monitoring;

a recording system arranged to record at first and second instants in time, respectively, first and second image data representing at least a portion of said projected pattern on the object, said first and second image data being representative of a three dimensional configuration of said object at said first and second instants in time, respectively; and a processing system arranged to process said first and second image data to generate differential data representative of a change in the configuration of said object between the first and second instants in time.

Preferably, the recording system is arranged to record a plurality of images of at least a portion of the projected pattern of radiation at one instant in time to record image data representative of a three dimensional configuration of the object, each of the plurality of images being recorded at a different viewpoint of said object.

In a preferred embodiment the apparatus comprises a pattern generator arranged to generate said pattern of radiation for projection by the projection system.

The pattern generator may be arranged to generate at least one calibration pattern for projection onto the object for monitoring and/or a calibration object.

The projection system may be arranged to project a pattern of radiation of non-ionising electromagnetic radiation.

The projection system may be arranged to project the pattern of radiation as visible radiation and the recording means is arranged to detect visible radiation.

The projection system may alternatively be arranged to project the pattern of radiation as infrared radiation and the recording system may be arranged to detect infrared radiation.

Further, the pattern may be a spatially-varying intensity pattern, which may comprise a combination of spatially distributed crossing points, corners and/or circular patches.

Further features and advantages of the invention will become apparent from the following description of preferred embodiments of the invention, given by way of example only, which is made with reference to the accompanying drawings.

BRIEF DESCRIPTION OF THE DRAWINGS

FIG. 6 shows a monitoring apparatus with a plurality of projection systems in accordance with a fourth embodiment of the present invention;

FIG. 7 shows a calibration pattern of radiation being projected onto a known object;

FIGS. 8A and 8B show different patterns of radiation being projected onto an object;

DETAILED DESCRIPTION OF THE INVENTION

The contents of U.S. patent application Ser. No. 13/157,672 filed Jun. 10, 2011 and PCT/EP2009/066790 filed Dec. 10, 2009 are incorporated by reference in their entirety herein.

The present invention relates to a method of monitoring an object and an apparatus for performing the method. Further, the invention relates to computer software arranged to perform the method of the invention, and to a data carrier storing such software. In the exemplary embodiments disclosed hereinbelow reference is made to a method of monitoring a configuration indicative of a lung function of a person, by monitoring a change in volume of a thorax of a person. Such a method is a non-contact, non-invasive method that can safely monitor chest and abdomen dynamic volume changes and accurately derive air flow and lung function data to assist medical diagnosis and patient care. Lung function of a person includes, but is not limited to, thoracic volume, respiratory rate, tidal volume, inspiratory and expiratory times, forced spirometry, regional changes in chest wall movement and regional lung function. Other applications of the invention are envisaged, as explained below.

Figure 1:
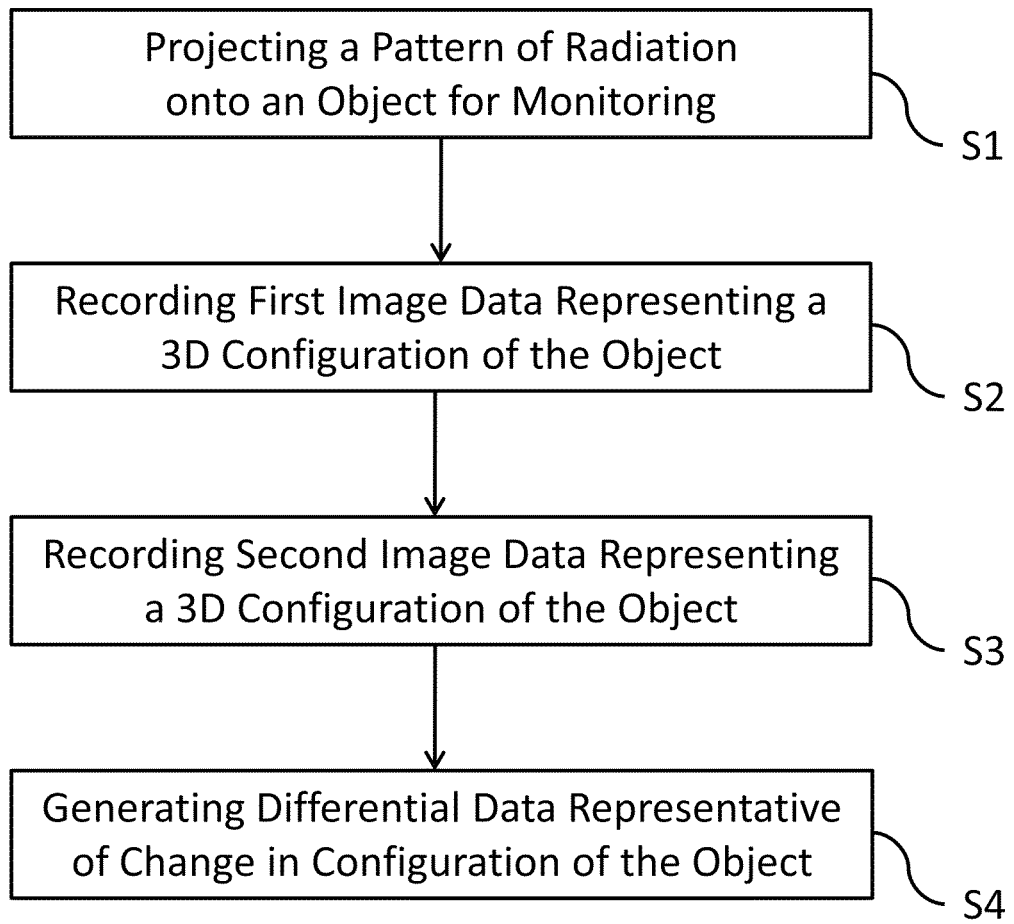
FIG. 1 shows a flow diagram giving an overview of the method of the present invention.

With reference to FIG. 1, which shows a flow diagram giving an overview of the method of the present invention, a pattern of radiation is projected onto an object that is to be monitored in step S1.

In step S2, first image data is recorded at a first instant in time. The first image data is representative of at least a portion of the pattern of radiation projected onto the object and contains data representative of a three dimensional configuration of the object at the first instant in time.

In step S3, second image data is recorded at a second instant in time, different from the first instant in time. The second image data is representative of at least a portion of the pattern of radiation projected onto the object and contains data representative of a three dimensional configuration of the object at the second instant in time.

In step S4, the first and second image data is processed to generate differential data that is representative of a change in the configuration of the object between the first and second instants in time. The change in configuration may be a zero change if the object configuration does not change between the first and second time instants.

Monitoring a configuration of an object in this manner has the advantage of being usable to provide an accurate computer generated representation of the object over time without the need of making physical contact with the object. Further, the method of the invention allows monitoring of a change of a configuration of the object using the differential data, which may, for example, represent a change of surface shape, position, volume and/or a three dimensional shape of an object being monitored. Further, the method of the invention may be applied to monitor a change of configuration of a part of an object, rather than of the whole object.

As will be explained further below, the method of the invention may optionally include: recording further image data representing at least a portion of the projected pattern of radiation on the object at a plurality of further instants in time, the further image data being representative of a three dimensional configuration of the object at each of the plurality of further instants in time; processing the further image data to generate differential data representative of a change in the configuration of the object between at least two of the plurality of further instants in time.

Figure 2:
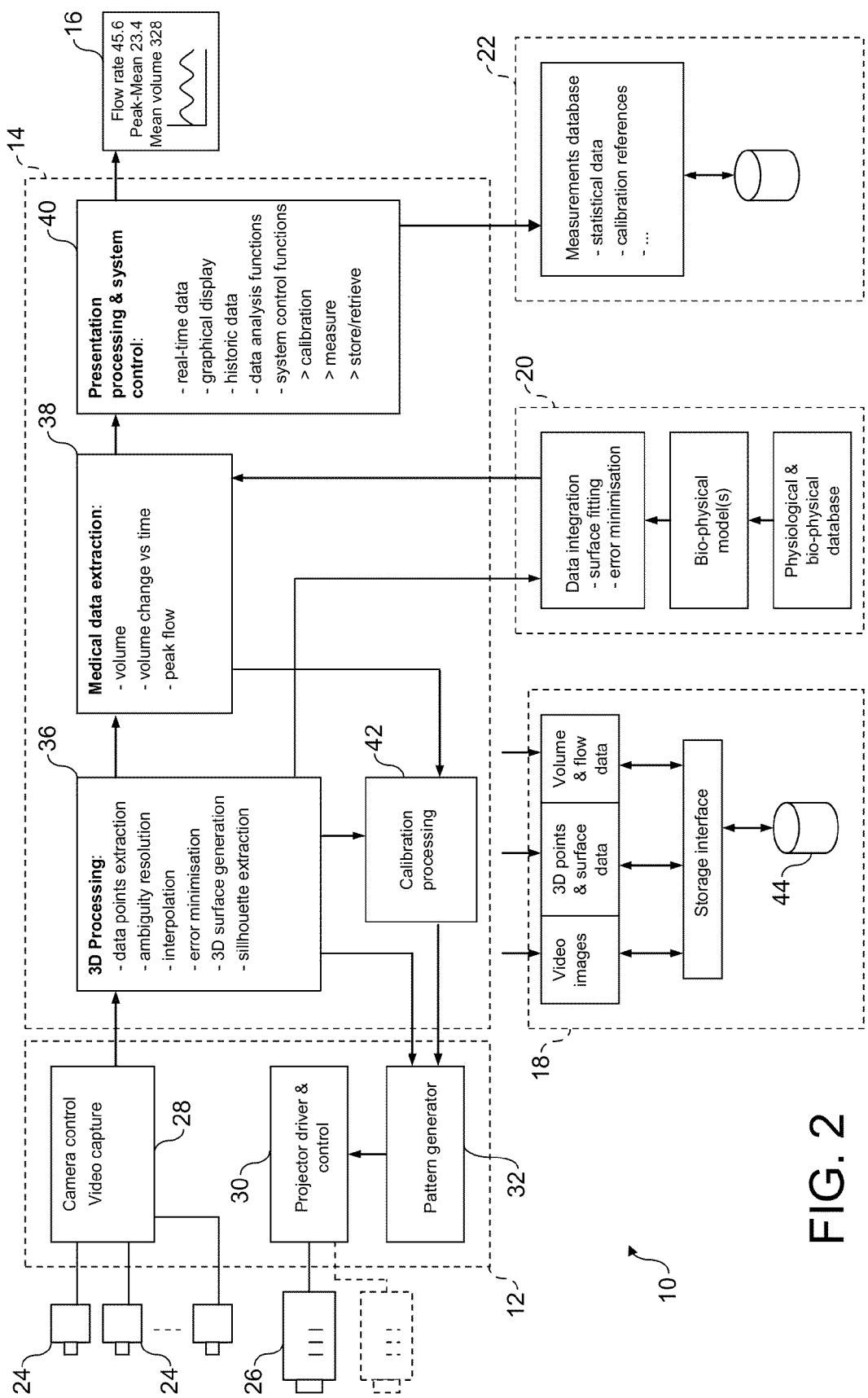
FIG. 2 shows a block diagram of a monitoring apparatus in accordance with an embodiment of the present invention.

FIG. 2 shows a block diagram of apparatus arranged to perform the method of the invention, in accordance with an embodiment of the present invention. The apparatus 10 comprises a scanning system 12, data processing and a man machine interface (MMI) system 14, a display system 16, image data storage system 18, bio-physical modeling data 20 and a statistical database 22.

The scanning system 12 includes a recording system 24, including for example at least two video cameras, at least one projection system 26, for example, a video projector, video capture hardware 28 for controlling the recording systems 24 and capturing an image from each of the recording systems 24, interface system 30 for connecting a processing platform, for example a personal computer (PC) to the projection system 26, and a pattern generator 32 for creating at least one pattern for the projection system 26.

In one embodiment of the present invention the monitoring apparatus 10 may comprise two 200 Hz, 640×480 resolution cameras 24 and a video projector 26, all mounted on an adjustable mounting rig so as to define the relative positioning of the cameras 24 and the video projector 26. Both the cameras 24 and the video projector 26 may be controlled by a standard personal computer (PC) platform incorporating a video capture card for the cameras 24 and a graphics card to drive the video projector 26. In other embodiments, the camera itself may at least partly process recorded image data, for transmitting to a further processor, such as of a standard PC, via a digital bus connection, such as Universal Serial Bus (USB), Firewire™ or an Ethernet connection.

The apparatus of the present invention is advantageous in that the precise geometric positioning and separation of the projection and recording systems with respect to each other, and to the object being monitored, is flexible; i.e. precise positioning is not required. The calibration of the projecting and recording systems, as described later, allows the physical positioning of the projecting and recording systems to be taken into account to generate accurate data.

Since each camera of the recording system may be arranged at a different viewpoint of the object, and can record an image of the projected pattern at a certain time instant, the combination of the images recorded at that certain time instant by the different cameras allows a greater proportion of the object to be monitored. In this way, the cameras can be arranged to provide greater coverage of the object, for example by positioning one camera to capture part of the object which another camera cannot accurately capture due to blind spots for example. Accordingly, the image data recorded for each time instant is representative of a greater part of the object, and therefore allows more accurate data to be generated for the object between different time instants.

The data processing and MMI (man machine interface) system 14 comprises four main elements: three dimensional processing system 36, medical data extraction system 38, presentation processing and system control system 40, and calibration processing system 42.

The presentation processing and system control system 40 performs processing to allow control by a user of the monitoring apparatus 10, and may present results via the display system 16. Presentation processing and control is performed in conjunction with the image and data storage processing system 18, by which data from the recording system 24 recording images, image data from the 3D processing, derived medical data, and other intermediate computation results may be stored and retrieved via a storage device 44. The storage device 44 may be a computer disk or solid-state storage device.

In performing the method of the present invention, the projection system 26 projects, otherwise referred to herein as scanning, one or more patterns of radiation onto an object for monitoring and each camera of the recording system 24 simultaneously captures, at different viewpoints, an image representative of at least a portion of the at least one projected pattern of radiation as it appears on the object. In this way, a plurality of images of the same and/or different portions of the projected pattern may be recorded at one instant in time. The captured image from each camera of the recording systems 24 is then processed and recorded as image data that is representative of a three dimensional configuration of the part of the object on which the corresponding pattern portion was projected at that instant in time; such as for recording the first image data for the first time instant. The image data recorded at the second time instant, and for any further time instants, such as consecutive third and fourth time instants, may be recorded in a similar manner by recording and processing a plurality of images of the object at the particular time instant. The simultaneous capture of an image by each camera of the recording system 24 at a time instant ensures data points between the image data for the different images can be accurately correlated during further data processing. The captured images may be processed using known image processing techniques, to reduce noise, for example.

The at least one pattern of radiation may include a spatially-varying intensity pattern comprising a combination of distinct and readily locatable pattern elements, for example a combination of spatially distributed crossing points, corners or small circular patches. For example, the at least one pattern of radiation projected on to the object may comprise tessellated combinations of lines and points. The pattern may include non-illuminated pattern patches, spaced in between illuminated patches of the pattern. The pattern elements appear distorted when projected on the object, and this distortion allows three-dimensional configuration data of the part of the part of the object upon which the pattern elements are projected, such as the first or second image data, to be derived from the captured image data; this method of scanning an object is commonly referred to as a structured light technique. The pattern of radiation may be a simple repeated pattern and/or may be selected with a complex repeating pattern of features such as spots, light/dark edges, for example, in order to avoid ambiguity in the images of the pattern recorded by the cameras, and to capture higher resolution images of the object. Ambiguity occurs when a part of the pattern falling on the object is distorted in a way so as to appear the same as if the object was not there. Such ambiguity makes it difficult to determine accurately a configuration of the object. In other embodiments, a sequence of different radiation patterns may be projected onto the object, each of the different patterns being projected consecutively at a different instant in time. The projection system 26 may project the pattern of radiation of certain selected wavelengths, for example visible radiation or invisible infrared radiation onto the object, although it is envisaged that the pattern radiation may be of other wavelengths of the spectrum of non-ionising and electromagnetic radiation. Accordingly, the recording system 24 is adapted to capture the projected radiation of the appropriate wavelength(s). The projection system 26 requires a normal incoherent light source, rather than coherent laser illumination; this enables medically-safer scanning of a subject/object, for example a child, compared to a laser-based projection method.

The three dimensional processing system 36 processes the images captured by the recording system 24 and extracts image data representative of the three dimensional configuration of the object which correspond to equivalent points on the surface of the object. This processing may include image analysis to maximise useable contrast and dynamic range within the captured images, image noise reduction, location of specific features of the projected patterns of radiation, resolution of ambiguities in an expected location of specific pattern features due to pattern distortion by the object surface, suppression of data errors, and/or identification of silhouettes to assist tracking of gross movement of the object when monitoring the object over time. The image data is then interpolated to create continuous surface representations of the object being monitored.

The recording system 24 is arranged in embodiments of the invention to record the same portion of the pattern at each of the first and second instants in time. In this way, assuming the object remains stationary, the change in configuration of the same part of the object can be monitored at both the first and second instants. In other embodiments, the recording system 24 may be arranged to record a different portion of the projected pattern at the first and second time instants. This may for example allow image data to be recorded for the same part of the object being monitored, despite gross movement of the object part, and therefore a different part of the pattern falling on the object part under observation.

Tracking algorithms may be used for the image data processing to track larger (gross) movement of the object being monitored to improve the calculation accuracy of the image data by helping the discrimination of wanted motion for monitoring of the scanned surface(s) of the object from the overall (gross) movement of the object. The algorithms may also detect when the object is not within the field of view of the recording systems 24 and if the object is moving rapidly, for example, where the object is a person, the algorithm may be arranged such that coughing of the person may be considered as a gross movement.

In addition, the tracking algorithm may be used to determine when a gross movement of the object occurs and to indicate this to an end user, ignore image data occurring at those instants in time when the gross movement occurs or determine the new position of the object if, for example the object has geometrically moved position by rotation or translation.

The image data representative of the three dimensional configuration of the object may be used to obtain data indicative of a volume corresponding to the scanned object area by processing consecutive (sequential) image data produced by the three dimensional processing system 36 of the object. Differential data can be generated between the first and second image data taken at the respective first and second instants in time, which represents a change in configuration of the scanned object between the two instants in time. The differential data may be generated by comparing the first image data with the second image data, to identify differences between the three-dimensional configuration of the object at the first instant in time and the three-dimensional configuration of the object at the second instant in time. The differential data is indicative of these identified differences, and therefore represents a change in configuration of the object between the first and second instants. The two instants in time may be two consecutive points recorded in time; alternatively, the two instants may be any two instants recorded in a period of time, which may be separated by other time instants for which image data is recorded. Therefore, it is possible to track dynamically any changes in the configuration of at least part of the object between any two time instants and over a period of time encompassing a plurality of time instants. In embodiments where the object is a person the change in configuration may be representative of a change in the volume of at least part of the object, for example, a change of the volume of the chest and/or abdomen cavities.

Figure 3A:
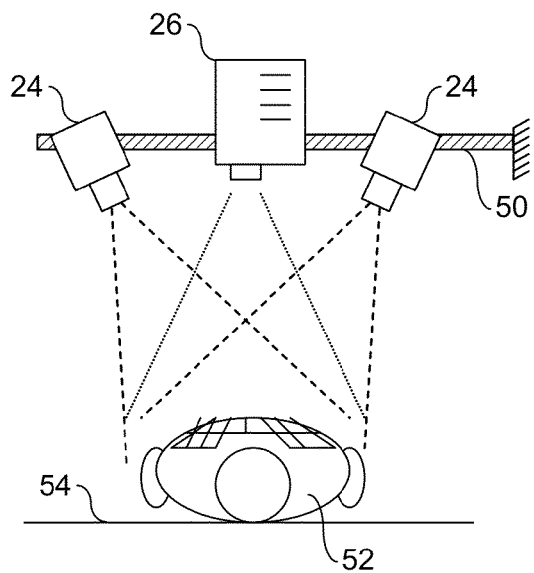
FIGS. 3a and 3b show a side view and an end view, respectively, of a monitoring apparatus in accordance with a first embodiment of the present invention.
Figure 3B:
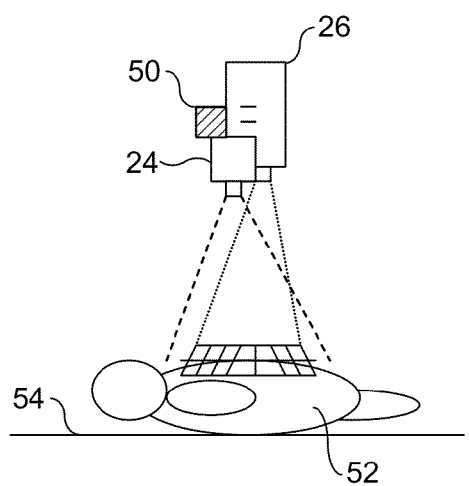
Figure 4:
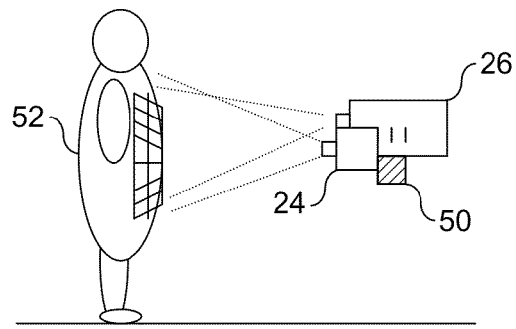
FIG. 4 shows a side view of a monitoring apparatus in accordance with a second embodiment of the present invention.

In embodiments where the apparatus is to be used in a medical environment, for example as shown in FIGS. 3, 4 and 5, referred to later, the medical data extraction system 38 performs an algorithmic computation to derive a volume change for the body part being monitored by the apparatus from the differential data.

To assist in determining a configuration change, such as a volume, of at least part of the object, an approximation of the volume of the scanned part of the object is calculated, by approximating the configuration of portions of the object part which are not visible to any of the recording systems 24 and/or which are not illuminated with the projected pattern of radiation. For example, if the pattern is projected upon a front side of a person's chest being monitored, the pattern does not fall upon the rear side of the person's chest, and the configuration of the rear side of the chest cannot be determined by recording image data of the rear side. However, the configuration of the rear side of the person's chest may be approximated to determine at least a crude, and more preferably a refined, configuration of the rear side of the chest. This approximately determined configuration of the object part without the projected pattern may be processed with the recorded image data, for example the first and second image data, to generate more accurate differential data for the change in configuration of the person's chest over time. The approximation may be determined using an interpolation algorithm for a flat surface. Alternatively, a more complex algorithm may be used to interpolate the configuration of the part without the projected pattern, for example using a shape more representative of the object part in question, in this case a person's chest. Such a representative shape may be part of a cylinder or a sphere, and/or may perhaps use bio-physical data, as described later, of the type of person, or indeed of the specific person being monitored, to refine the approximation. Using this approximated configuration in combination with the recorded image data derived from the image data captured for the scanned object part, a change in configuration, such as a volume of the object part being monitored, can be determined more accurately, providing more reliable image data representing the three dimensional configuration of the object, and differential data. This is important especially in applications of the method requiring a high level of data accuracy, for example in the medical field, when the generated data may be used to diagnose medical conditions and appropriate treatments. Moreover, for delicate objects such as ill patients, which cannot be easily moved, this approximation allows the patient to remain still, and lying on a bed for example, whilst still being able to determine accurate image data of the three dimensional configuration of the object and differential data.

Accordingly, processing of the data captured by the recording system 24 is used to create dynamic three dimensional models of the subject's body movement, volume, surface area and other similar physical parameters. The breathing and respiration rate can then be calculated by comparing concurrent data images to generate differential data that is representative of a change in volume.

Information may then be displayed to an end user in a numerical and/or graphical format via a display system, and/or may be transmitted via data network interfaces provided as part of the processing platform (e.g. personal computer) to other systems, for remote display or additional analysis. Output information can be categorised and used as part of a decision support process or expert system linked to clinical management and care schemes. As the reconstruction may provide a full three dimensional representation of the object, in some embodiments using the approximation of the object part not illuminated with the radiation pattern, it is possible to view the object surface on-screen from any novel viewpoint.

Breathing airflow relating to lung function can be computed from dynamic volume changes in the object's volume. This process may be augmented by comparison with data in the statistical database 22, which contains data from prior reference (trial) operations of the apparatus and/or from prior measurement operations of the apparatus on a number of different persons. In embodiments of the invention, the statistical database data provides standardised, statistically-averaged parameters for selected sets of persons according to selected granges of age, sex, weight and body types. Comparison using the statistical database data assists enhanced interpretation of computed dynamic volume changes as compared with statistical norms. The statistical database data may also be used to provide refinement of the scaling and reference parameters for the bio-physical model data 20.

The accuracy of volume calculations may be improved by the bio-physical modeling data 20, which integrates the image data recorded with a volumetric model of the object, using mapping and 'best fit' algorithmic processing, for example. The volumetric or bio-physical model data 20 comprises a 'physics-based' approximation of the anatomical structure of the object or subject being scanned and models the physical properties of the object area, for example, the physical and elastic properties of the chest/abdomen, and movement constraints due to joint and skeletal construction. The bio-physical model data 20 is based on generic models for the object under consideration with physical modeling parameters adjusted and calibrated according to average values according to subject type, age, sex, body mass and/or other configurations. The bio-physical model data can include stored data from prior reference (trial) operations.

FIGS. 3a and 3b show exemplary parts of the monitoring apparatus in accordance with an embodiment of the present invention. The apparatus 10 comprises first and second cameras as part of the recording system 24, which may be, for example, Allied Vision Technology Pike F032B cameras, and the projection system 26, which may be, for example, an Acer P1625 projector, attached to a mounting frame 50. The angle that each of the recording systems 24 is mounted with respect to the mounting frame 50 may vary from about 10 degrees to about 40 degrees and depends on the distance from the recording system 24 to the object 52. In this embodiment it can be seen that the projection system 26 projects a pattern of radiation onto the chest and abdominal area of a subject 52 laying prone on a surface 54. The projection rate may be for example around 50 or 60 Hz, or 180 Hz or 360 Hz. The recording rate from the recording system 24 is consistent with the projection rate, for example if the projection rate is 180 Hz, the recording rate would also be 180 images per second for each of the first and second recording systems. Other projection and recording rates of the first, second and further image data is envisaged within, but not limited to, the range of 50 to 360 Hz; therefore, the projection and recording rates may be slower or faster than rates of 50 or 360 Hz. The first and second cameras of the recording system 24 may be orientated so that the field of view of one of the recording system completely or at least partially overlaps the field of view of the other recording system. The apparatus 10 may be arranged for monitoring and diagnosis of, for example, adults, children, premature infants, non-cooperative subjects or where any form of contact method is impractical, for example, premature infants, burns victims, critical care patients. The apparatus 10 may be arranged so that the subject can be monitored in an upright standing position as illustrated in FIG. 4.

Figure 5A:
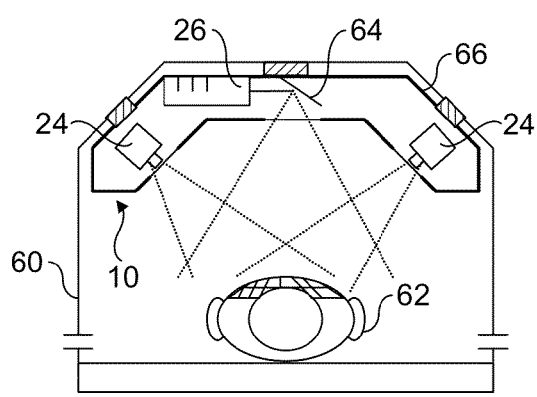
FIGS. 5a and 5b show monitoring apparatus incorporated as part of an incubator in accordance with a third embodiment of the present invention.
Figure 5B:
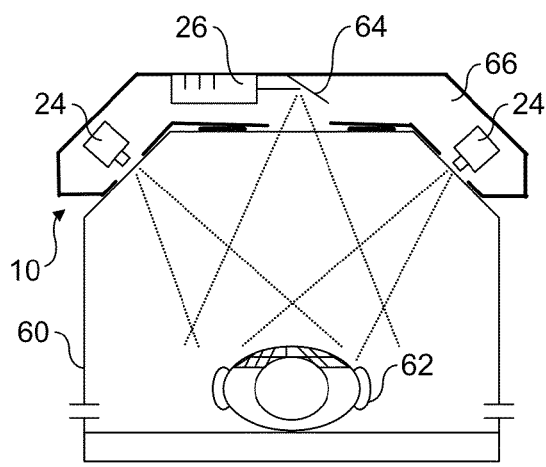

Referring now to FIG. 5a, there is shown an embodiment of parts of monitoring apparatus 10 in accordance with the present invention incorporated an incubator for a baby. The monitoring device 10 comprises a projection system 26 arranged to project radiation onto an reflective optics device 64, for example a mirror, which reflects the radiation emitted from the projection system onto a baby 62 located in the incubator 60, and two cameras of a recording system 24. The monitoring apparatus 10 is mounted in a sealed housing 66 and mounted to an interior portion surface of the incubator 60 as shown in FIG. 5a. It will be appreciated that the monitoring apparatus 10 may be arranged to be located on an exterior surface of the incubator 60 as shown in FIG. 5b.

FIG. 6 shows a set up of monitoring apparatus for performing the method of the invention, according to a further embodiment. A plurality of patterns of radiation may be projected onto the object simultaneously, so that a greater coverage of the object being monitored is achieved. Accordingly, as shown in FIG. 6, more than one pattern of radiation is projected onto the object, using the three projectors, onto two opposite sides of the object and onto a surface between the two opposite sides. Two cameras, arranged between the three projectors, each simultaneously record image data of the projected patterns at each of different instants in time, for processing to derive differential data.

In use the apparatus of FIGS. 3, 4, 5 and 6 may be set-up in a specific configuration for the environment and/or object to be monitored. The apparatus may be calibrated in order to perform the method of the invention with an acceptable level of accuracy. The method of the invention includes calibrating the apparatus for performing the invention. The calibration includes projecting a calibration pattern of radiation onto a calibration object; and recording calibration image data representing at least a portion of the projected calibration pattern of radiation, the calibration image data being representative of a three dimensional configuration of the calibration object. The first and second image data in step d) may be processed with the calibration image data to generate the differential data based on the calibration. According to such calibration, in embodiments of the invention, two types of calibration may be conducted: projector and recording system calibration, and unit calibration.

Projector and recording system calibration may be performed automatically and continuously during monitoring a change of configuration of the object, described previously. This may be achieved by projecting one or more calibration patterns onto the object being monitored as part of projecting the radiation pattern onto the object for monitoring. The object being monitored may therefore be considered to be a calibration object. The calibration pattern may be projected on the calibration object, and the calibration image data recorded, at one or a plurality of time instants different from the first and second time instants. For example, the calibration pattern may be projected immediately before the first time instant, and immediately before the second time instant, so that the calibration data is indicative of the projector and recording system characteristics at the first and second time instants, without performing the calibration simultaneously as recording the image data for monitoring the object. In this way the calibration pattern(s) and the pattern for the object monitoring may be interleaved with each other over time. The recorded first and/or second image data may then be processed using recorded calibration image data representative of, in three-dimensional space, characteristics of the projector system and parts of the recording system, for example of the cameras, such as their relative positions and optical focal points. This improves the accuracy of the first and/or second image data.

By appropriate selection of the timing of projecting, and recording of image data of, the calibration pattern(s) and the pattern(s) for object monitoring, the projector and recording system calibration may be performed rapidly such that it may be near-simultaneous with object monitoring. Accordingly, characteristics of the projector system and parts of the recording system, for example optical characteristics and/or relative positioning of the projector and cameras, may be repeatedly determined during object monitoring, without needing to halt object monitoring. In this way small changes over time in such characteristics, for example due to a drift in focus, zoom factor and/or angular positioning of the projector and/or recording systems, may be determined by the projector and recording system calibration process and thereby used to correct the image data generated from monitoring the object. Movement of the object being monitored does not affect the calibration of the projector and recording system. Object movement can be dealt with using tracking algorithms for example, described above.

Unit calibration is preferably conducted before monitoring of an object according to the invention method, described with reference to FIG. 1, is begun. The unit calibration is used to determine absolute measurements accurately for when monitoring the object and involves determining at least one absolute distance, so that during calibration all the distances between the projector system, parts of the recording system and the location where the object for being monitored will be placed, such as a bed in the example that the object is a person, may be accurately determined from the calibration image data and/or any differential data generated therefrom during calibration, for example between calibration image data at different time instants. Once the apparatus is set up for the monitoring procedure, the unit calibration is performed by projecting a calibration pattern of radiation, generated by the projection system, onto a calibration object of known dimensions, and recording image data of the calibration object using the recording system. Since the dimensions of the calibration object are known, the calibration system 42 can determine the absolute positions of the recording and projection systems. Accordingly, the calibration system 42 can determine a unit scale for dimensional units, against which image data recorded during monitoring of the invention method can be compared, so that absolute dimensions of the object being monitored can be accurately determined. For example, a height and/or a width in centimeters of at least part of an object being monitored can be accurately measured by comparing object dimensions derived from the image data of the object with the unit scale. From this, volume measurements in liters for example, of a part of the object being monitored may be calculated. By accurately being able to take measurements of the object during monitoring, the differential data may be generated with a high level of accuracy.

The calibration object may have three points of known relative position and distance visible in the field of view of the recording system. The calibration object could, as an example, be in the form of a 'wand' waved over a patient before the monitoring begins, or a known printed or projected pattern of precise dimensions on the table, chair or bed on which the patient lies, which is used to brace the patient's back. The calibration object may of course in other embodiments be other objects of known dimensions.

The unit calibration may be conducted only once, assuming that the physical set up and positioning of the monitoring apparatus is not changed. If the physical set up is changed, the unit calibration will need to be conducted again.

For either, or both, the projector and recording system calibration, and the unit calibration, the calibration pattern may be similar, or the same, as the pattern of radiation described previously for the monitoring method. FIG. 7 shows an exemplary calibration pattern projected onto a saline bag. Further, in other embodiments, the calibration pattern may include a sequence of different calibration patterns projected consecutively onto the calibration object, and recording calibration image data for each of the different patterns. For example, the sequence of patterns may include a number of distinct patterns, typically about sixteen for example, projected in rapid sequence onto the object. The forms of the patterns can be arranged to provide successively finer pitched features within the patterns. The projected patterns of radiation may be, but are not restricted to, a generic form of a simple pattern which is repeated (tessellated) in both horizontal and vertical (X and Y) directions. Further, in other embodiments, for the projector and recording system calibration, the calibration pattern may be interleaved with the pattern projected onto the object during the monitoring method. In other embodiments, projector and recording system calibration image data may be derived from the first and/or second image data; the projected pattern for object monitoring may include pattern characteristics for use in such calibration.

Figure 9:
FIG. 9 shows a pattern of radiation projected onto a model of an infant.
Figure 10:
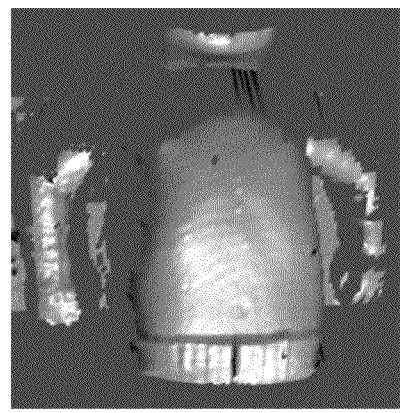
FIG. 10 shows an interpolated three-dimensional representation of the model of the infant shown in FIG. 9 created in accordance with the method of the present invention.

As shown in FIGS. 8A, 8B and 9, one or more patterns of known structure (including but not restricted to regular structures such as lines or points) may then be projected onto the object, after unit calibration, to start the monitoring of the object. These patterns may be fine or coarse or a combination of both depending on requirements for system size, accuracy and fields of view.

The recording system 24 then captures images of the area(s) of the object, as explained previously, and the patterns of structured radiation as they appear on the object, capturing information representative of object configuration, for example, surface shape, movement and three dimensional configuration shape.

The above embodiments are to be understood as illustrative examples of the invention. Further embodiments of the invention are envisaged.

Further embodiments of the method are envisaged which include recording further image data representing at least a portion of the projected pattern of radiation on the object at a plurality of further instants in time, such as consecutive third and fourth instants in time. The further image data may comprise a plurality of image data recorded successively at a plurality of time instants after the first and the second time instants, which represent a three dimensional configuration of the object at the respective further instants in time. The further image data is processed to generate differential data representative of a change in the configuration of the object between at least two of the plurality of further instants in time. The properties of the further image data may be similar to those of the first and second image data described above. Accordingly, the further image data may be recorded, processed and/or used in a similar manner as any recording, processing and/or use of the first and/or second image data described previously. In this way, the method of the invention can monitor a change in configuration, such as a volume, of the object over a period of time spanning the first, second and further instants in time. Accordingly, the configuration change of an object may be monitored continuously.

In further exemplary embodiments, the monitoring apparatus described above may be used for animal monitoring and veterinary care, data capture for body research, bio-modeling, and avatar animation, in addition to other applications where monitoring of a three dimensional configuration of an object is required.

Further, the method of the invention may monitor breathing and other life signs in, for example, a hospital, medical centre or local practice environments or in mobile environments, for example, paramedic/ambulatory, field hospitals (civilian, military) or disaster recovery centres.

The projection system may include a light source (e.g. a collimated LED source) illuminating a set of optical patterns created on a physical medium, for example film or glass, and sequenced via mechanical system, for example a rotated wheel on which the patterns are mounted and which is positioned in front of the light source.

The angular field of view may be increased by using more than two recording systems and more than one projecting system so that more surface area of the object/subject may be captured and ensuring that the area to be captured has at least two of the n cameras deployed. FIG. 6 illustrates one configuration to enhance scanning coverage of the subject/object.

As described above, a three dimensional representation of at least part of the object can be derived using the plurality of images captured at one time instant of the projected pattern on the object, using for example two cameras. By taking a plurality of images for one time instant, image data with a greater coverage of the object, and/or with reduced occlusion problems of a certain object part, can be obtained. In other advantageous embodiments of the invention, the recording system may include only one camera which records one image of at least a portion of the projected pattern on the object at the first and second, and possibly further, time instants. A three dimensional representation of at least part of the object may be derived for each time instant by interpreting the recorded pattern in each respective image. Accordingly, in such embodiments, multiple cameras are unnecessary.

The apparatus may comprise the recording system and projection system and the image data captured by the recording system may be provided in a suitable form for processing, to generate the image data representative of the three dimensional configuration and the differential data. Such processing of the image data may be processed remotely from the recording and projection systems and as such the processing system may be located in another room or may be located in another country, connected to the recording and projection system via a computer network, and arranged to receive the image data from the recording and projection system which are arranged to provide the image data to the processing system.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method of monitoring a regional lung function of a person, the method including the steps of:
    a) projecting a pattern of radiation onto at least a portion of the person for monitoring;
    b) recording at a first instant in time first image data from at least two video cameras disposed at different viewpoints toward said portion of the person, said first image data representing at least a portion of said projected pattern of radiation on the portion of the person at said different viewpoints, said first image data being representative of a three dimensional configuration of said portion of the person at said first instant in time;
    c) recording at a second instant in time second image data from said at least two video cameras, said second image data representing at least a portion of said projected pattern of radiation on the portion of the person at said different viewpoints, said second image data being representative of a three dimensional configuration of said portion of the person at said second instant in time; and
    d) processing said first and second image data to generate differential data representative of a change in volume of said portion of the person between the first and second instants in time to determine the regional lung function of the person.

2. A method according to claim 1, wherein the portions in steps b) and c) are substantially the same portion of the pattern, or wherein the portions in step b) and c) are different portions of the pattern.

3. A method according to claim 2, wherein the method includes processing the first and second image data to identify gross movement of the portion of the person between the first and second instants in time.

4. A method according to claim 1, wherein in step a) a sequence of different patterns of radiation is projected onto the portion of the person, each of the different patterns being projected consecutively at a different instant in time.

5. A method according to claim 1, including:
    recording further image data representing at least a portion of the projected pattern of radiation on the portion of the person at a plurality of further instants in time, said further image data being representative of a three dimensional configuration of said portion of the person at each of the plurality of further instants in time;
    processing said further image data to generate differential data representative of a change in the volume of said portion of the person between at least two of said plurality of further instants in time.

6. A method according to claim 5, wherein the further image data is recorded at a rate of 50 to 360 instants in time per second.

7. A method according to claim 1, wherein the method includes approximating the configuration of a portion of the portion of the person upon which the patient of radiation is not projected.

8. A method according to claim 7, wherein the method includes using the first and/or second image data for said approximating.

9. A method according to claim 7, wherein the method includes generating the differential data using said approximated configuration of the portion of the portion of the person.

10. A method according to claim 1, wherein the method includes processing said first and second image data with bio-physical model data characterizing the person.

11. A method according to claim 10, wherein the bio-physical model data includes parameters representative of size, age, sex and/or body type of the person.

12. A method according to claim 1, wherein the method further includes calibrating of apparatus arranged to perform at least steps a) and b), said calibrating including: projecting a calibration pattern of radiation onto a calibration object; and recording calibration image data representing at least a portion of said projected calibration pattern of radiation, said calibration image data being representative of a three dimensional configuration of said calibration object, and processing said first and second image data in step d) with the calibration image data to generate the differential data.

13. A method according to claim 12, wherein the projecting in step a) further includes projecting said calibration pattern, or at least one of said calibration patterns onto the object for monitoring, and the first and/or second image data recorded in steps b) and/or c) include calibration image data representative of characteristics of a projection system and recording system of apparatus for performing said method.

14. A method according to claim 13, wherein the projected pattern of radiation and the projected calibration pattern or at least one of the calibration patterns are interleaved with each other.

15. A method of monitoring a regional lung function of a person, the method including the steps of:
   a) projecting a pattern of radiation onto at least a portion of the person for monitoring;
   b) recording at a first instant in time first image data from at least two video cameras disposed at different viewpoints toward said portion of the person, said first image data representing at least a portion of said projected pattern of radiation on the portion of the person at said different viewpoints, said first image data being representative of a three dimensional configuration of said portion of the person at said first instant in time;
   c) recording at a second instant in time second image data from said at least two video cameras, said second image data representing at least a portion of said projected pattern of radiation on the portion of the person at said different viewpoints, said second image data being representative of a three dimensional configuration of said portion of the person at said second instant in time; and
   d) processing said first and second image data to generate differential data representative of a change in volume of said portion of the person between the first and second instants in time to determine the regional lung function of the person.

16. A method of monitoring a regional lung function of a person, the method including:
   a) receiving first and second image data recorded by the method of:
      i) projecting a pattern of radiation onto at least a portion of the person for monitoring;
      ii) recording at a first instant in time the first image data from at least two video cameras disposed at different viewpoints toward said portion of the person, said first image data representing at least a portion of said projected pattern of radiation on the portion of the person at said different viewpoints, said first image data being representative of a three dimensional configuration of said portion of the person at said first instant in time; and
      iii) recording at a second instant in time the second image data from said at least two video cameras, said second image data representing at least a portion of said projected pattern of radiation on the portion of the person at said different viewpoints, said second image data being representative of a three dimensional configuration of said portion of the person at said second instant in time, and
   b) processing said first and second image data to generate differential data representative of a change in the volume of said portion of the person between the first and second instants in time to determine regional lung function of the person.

17. A method of monitoring a regional lung function of a person, the method including the steps of:
   a) at a first instant in time, projecting a pattern of radiation onto at least a portion of the person for monitoring;
   b) recording at the first instant in time first image data from at least two video cameras disposed at different viewpoints toward said portion of the person, said first image data representing at least a portion of said projected pattern of radiation on the portion of the person at said different viewpoints, said first image data being representative of a three dimensional configuration of said portion of the person at said first instant in time;
   c) at a second instant in time, projecting a different pattern of radiation onto the portion of the person for monitoring;
   d) recording at the second instant in time second image data from said at least two video cameras, said second image data representing at least a portion of said projected pattern of radiation on the portion of the person at said different viewpoints, said second image data being representative of a three dimensional configuration of said portion of the person at said second instant in time; and
   d) processing said first and second image data to generate differential data representative of a change in volume of said portion of the person between the first and second instants in time to determine the regional lung function of the person.

18. An apparatus for monitoring a regional lung function of a person, the apparatus comprising:
   a projection system arranged to project a pattern of radiation onto at least a portion of the person for monitoring;
   a recording system comprising at least two video cameras disposed at different viewpoints toward said portion of the person, said at least two video cameras being arranged to simultaneously record at first and second instants in time, respectively, first and second image data representing at least a portion of said projected pattern on the portion of the person, said first and second image data being representative of a three dimensional configuration of said portion of the person at said first and second instants in time, respectively; and
   a processing system arranged to process said first and second image data to generate differential data representative of a change in the volume of said portion of the person between the first and second instants in time to determine regional lung function of the person.

19. An apparatus as claimed in claim 18, wherein the recording system is arranged to record a plurality of images of at least a portion of the projected pattern of radiation at one instant in time to record image data representative of a three dimensional configuration of the portion of the person, each of the plurality of images being recorded at a different viewpoint of said portion of the person.

20. An apparatus according to claim 19 comprising a pattern generator arranged to generate said pattern of radiation for projection by the projection system.

21. An apparatus according to claim 20, wherein the pattern generator is arranged to generate at least one calibration pattern for projection onto the portion of the person for monitoring and/or a calibration object.

22. Apparatus for monitoring a regional lung function of a person comprising:
a projection system arranged to project a pattern of radiation onto portion of the person at a first instant in time and at a second instant in time; and
a recording system comprising at least two video cameras disposed at different viewpoints toward said portion of the person, said at least two video cameras being arranged to simultaneously record at the first instant in time first image data representing at least a portion of the pattern projected on the portion of the person at the first instant in time and to record at the second instant in time second image data representing at least a portion of the pattern projected on the portion of the person at the second instant in time, said first and second image data being representative of a three dimensional configuration of said portion of the person at said first and second instants in time, respectively, herein the apparatus is operable to provide said first and second image data to a processing system operable to process said first and second image data to generate differential data representative of a change in the volume of said portion of the person between the first and second instants in time to determine the regional lung function of the person.

23. Apparatus for monitoring a regional lung function of a person comprising:
a processing system arranged to process first and second image data to generate differential data representative of a change in the volume of at least a portion of the person between a first and a second instant in time to determine the regional lung function of the person, wherein the apparatus is operable to receive said first and second image data from further apparatus comprising:
a projection system arranged to project a pattern of radiation onto portion of the person at a first instant in time and at a second instant in time; and
a recording system comprising at least two video cameras disposed at different viewpoints toward said portion of the person, said at least two video cameras being arranged to simultaneously record at the first instant in time the first image data which represents at least a portion of the pattern projected on the portion of the person at the first instant in time and to simultaneously record at the second instant in time the second image data which represents at least a portion of the pattern projected on the portion of the person at the second instant in time, said first and second image data being representative of a three dimensional configuration of said portion of the person at said first and second instants in time, respectively.

24. A computer program product comprising a non-transitory computer-readable storage medium having computer readable instructions stored thereon, the computer readable instructions being executable by a computerized device to cause the computerized device to perform the method of claim 1.

25. A computer program product comprising a non-transitory computer-readable storage medium having computer readable instructions stored thereon, the computer readable instructions being executable by a computerized device to cause the computerized device to perform the method of claim 15.

26. A computer program product comprising a non-transitory computer-readable storage medium having computer readable instructions stored thereon, the computer readable instructions being executable by a computerized device to cause the computerized device to perform the method of claim 16.

27. A method according to claim 1, wherein:
the first image data recorded at step b) further represents a different portion of said projected pattern of radiation on a different portion of the person, said first image data being further representative of a three dimensional configuration of the different portion of the person at said first instant in time;
the second image data recorded at step c) further represents the different portion of said projected pattern of radiation on the different portion of the person, said second image data being further representative of a three dimensional configuration of the different portion of the person at said second instant in time; and
the differential data generated at step d) is further representative of a change in volume of the different portion of the person between the first and second instants in time.

28. A method according to claim 27, wherein:
the portion of the person comprises an abdomen; and
the different portion of the person comprises a chest.

29. An apparatus according to claim 18, wherein:
the first image data further represents a different portion of said projected pattern of radiation on a different portion of the person, said first image data being further representative of a three dimensional configuration of the different portion of the person at said first instant in time;
the second image data further represents the different portion of said projected pattern of radiation on the different portion of the person, said second image data being further representative of a three dimensional configuration of the different portion of the person at said second instant in time; and
the differential data is further representative of a change in volume of the different portion of the person between the first and second instants in time.

* * * * *